United States Patent [19]

Sato et al.

[11] Patent Number: 5,181,516
[45] Date of Patent: Jan. 26, 1993

[54] INTERNAL PRESSURE MEASURING DEVICE USING CATHETER WITH MULTIPLE LUMENS

[75] Inventors: Masamitsu Sato, Akita; Masami Tanishima, Tokyo, both of Japan

[73] Assignee: Nihon Kohden Corporation, Shinjuku, Japan

[21] Appl. No.: 748,083

[22] Filed: Aug. 1, 1991

[30] Foreign Application Priority Data

Aug. 27, 1990 [JP]  Japan ............................. 2-89301[U]
Nov. 5, 1990 [JP]  Japan ........................... 2-115404[U]

[51] Int. Cl.$^5$ .............................................. A61B 5/02
[52] U.S. Cl. .................................. 128/673; 128/748; 128/672; 73/708
[58] Field of Search ............... 128/674, 673, 748, 672, 128/675, 692, 650, 637; 73/708

[56] References Cited

U.S. PATENT DOCUMENTS 4,603,699  8/1986  Himpens ............................ 128/632
5,063,936  11/1991  Sato et al. ............................ 128/674

FOREIGN PATENT DOCUMENTS 2-19132  1/1990  Japan.
1440761  6/1976  United Kingdom ................ 128/675

Primary Examiner—Randall L. Green
Assistant Examiner—D. Willse
Attorney, Agent, or Firm—Hoffmann & Baron

[57] ABSTRACT

An internal pressure measuring catheter is constituted by at least three lumens which are: an internal pressure measuring lumen whose distal end is open and whose proximal end is connected to an internal pressure measuring transducer; a position correcting liquid-charged lumen whose distal end is closed, in which a liquid is charged, and whose proximal end is connected to a liquid pressure measuring transducer; and a position correcting atmosphere-opened lumen whose distal end is closed and whose proximal end is open to the atmosphere. The adjoining surfaces of the distal end portions of the liquid-charged and atmosphere-opened lumens have a small hole through which the charged liquid can be brought into contact with the atmosphere through the atmosphere-opened lumen. An internal pressure value is detected from the output signal of the internal pressure measuring transducer, and a head value corresponding to the height of the distal end of the charged liquid which is in contact with the atmosphere is detected from the output signal of the liquid pressure measuring transducer to correct the internal pressure value.

5 Claims, 3 Drawing Sheets

INTERNAL PRESSURE MEASURING DEVICE USING CATHETER WITH MULTIPLE LUMENS

BACKGROUND OF THE INVENTION

1) Field of the Invention

The present invention relates to an internal pressure measuring device for measuring an internal pressure in a living body using a catheter inserted into the living body from an electric signal output from a transducer connected to the proximal end of the catheter for converting the pressure into an electric signal.

2) Brief Description of the Prior Art

Examples of the above-described type of internal pressure measuring device include an invasive type blood pressure measuring device. When blood pressure measurements are conducted with this invasive blood pressure measuring device, zero adjustment is conducted prior to the measurements by opening the pressure-receiving surface of the transducer to the atmosphere in a state in which the atmosphere-opening point of the transducer is located at the same level or height as the pressure reference point, i.e., the heart (the tricuspid valve thereof), of the object to be measured.

However, this invasive type blood pressure measuring device has a vital drawback. That is, as the position of the object to be measured varies, the head of the blood in the catheter varies with respect to the transducer When the measured values are about several mmHg, as in the case of the central venous pressure, variations in the head of the blood may be about 0.73 mmHg/cm, which cannot be ignored. Hence, re-adjustment of the atmosphere-opening point of the transducer to the height of the pressure reference point is required for stably monitoring the blood pressure over a long period of time.

To obviate this problem, the present inventors disclosed in Japanese Patent Laid-Open No. 19132/1990 the internal pressure measuring device using a catheter with at least three lumens which are: the internal pressure measuring lumen whose distal end is open; the position correcting liquid-charged lumen whose distal end is closed and in which a liquid is charged; and the position correcting atmosphere-opened lumen whose distal end is closed, whose proximal end is made open to the atmosphere during the measurements, and having on the surface thereof which adjoins the distal end portion of the position correcting liquid-charged lumen a membrane which does not transmit liquid but transmits air. In this internal pressure measuring device, an internal pressure is detected from the signal output from the pressure measuring transducer mounted on the base and connected to the proximal end of the internal pressure measuring lumen. The internal pressure value is corrected using the head of the blood corresponding to the position of the membrane which is detected by the internal pressure measuring transducer connected to the proximal end of the liquid-charged lumen.

In the above internal pressure measuring device, since the distal end of the liquid-charged lumen is located at the same level as the pressure reference point, adjustment of the position of the pressure transducer, which would otherwise required when the measurement is started, is eliminated. Also, variations in the position which would occur thereafter can be automatically corrected. However, the above-described internal pressure measuring device has problems in that position measurement response is slow due to the use of the membrane and in that measurement errors may occur due to changes in the volume caused by changes in the temperature, e.g., in the body temperature, resulting from the difference in the coefficient of expansion between the liquid closed by the membrane and the liquid-charged lumen. The latter problem cannot be ignored particularly when a low pressure is measured by the device, as in the case of the central venous pressure.

SUMMARY OF THE INVENTION

Accordingly, an object of the present invention is to provide an internal pressure measuring device using a catheter with multiple lumens which is capable of correcting with a high degree of accuracy the effect of changes in the position of an object to be measured without being affected by the body temperature.

Another object of the present invention is to provide an internal pressure measuring device which includes a common zero adjustment circuit for both internal pressure measuring and liquid pressure measuring transducers.

This invention is characterized in that a small hole is formed on the adjoining surfaces of the distal end portions of the liquid-charged and atmosphere-opened lumens so as to bring the charged liquid into contact with the atmosphere through the atmosphere-opened lumen. The small hole may be formed by turning a single lumen to form the liquid-charged and atmosphere-opened lumens and by making the two lumens communicate with each other at the turned portion.

In this invention, since the distal end surface of the liquid-charged lumen which is in contact with the atmosphere is disposed at the pressure reference point, position adjustment of the pressure transducer is not required when the measurement is started. Also, variations in the position which would occur thereafter can be compensated for. Consequently, accurate internal pressure data can be monitored over a long period of time. Furthermore, since the distal end of the liquid-charged lumen is in direct contact with the atmosphere without using a liquid membrane, response is fast, and sufficient correction is thus made possible on variations in the position which may occur in a short period or in a vibrating fashion. Furthermore, as the body temperature changes, only the distal end surface of the charged liquid is displaced, and changes in the pressure value detected by the pressure measuring transducer is restricted to a minimum value. Particularly, accuracy of the pressure whose absolute value is low, as in the case of the central venous pressure, can be greatly improved.

The internal pressure measuring circuit portion includes a position correcting subtraction means for subtracting the output signal of the pressure measuring transducer from the output signal of the internal pressure measuring transducer, a zero adjustment value holding means for holding as a zero adjusting value the output signal of the subtraction means when the two transducers are zero adjusted, and a zero adjustment subtraction means for outputting an internal pressure signal by subtracting the zero adjusting value held by the zero adjusting value holding means from the output signal of the subtraction means which is output during the measurement. Consequently, common zero adjustment is made possible to the two pressure transducers. When the zero adjustment subtraction means and the position adjustment subtraction means are the same one, the zero adjustment circuit can further be simplified.

DETAILED DESCRIPTION OF THE INVENTION

Figure 1:
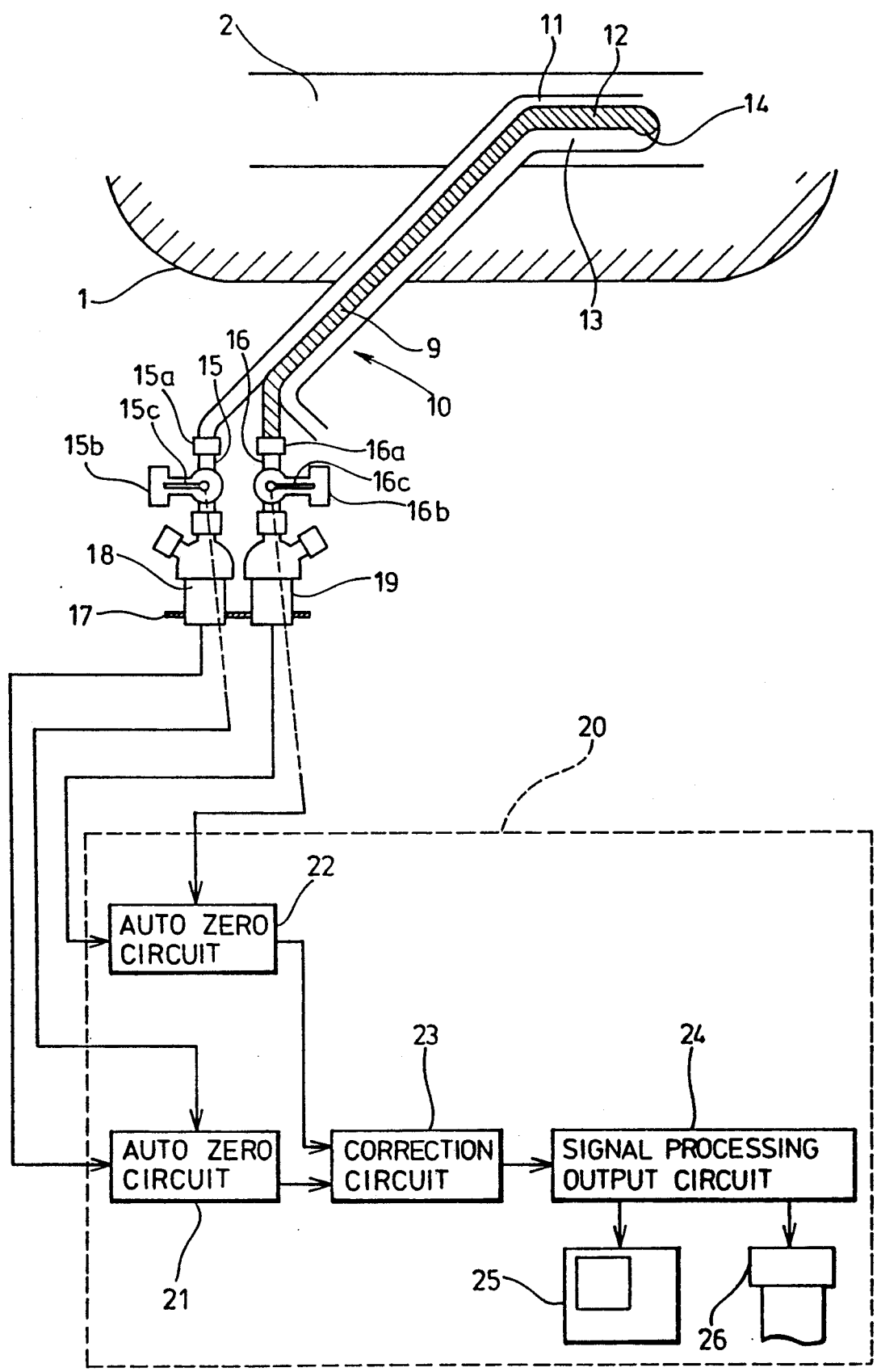
FIG. 1 is a cross-sectional view of a catheter of a first embodiment of an internal pressure measuring device according to the present invention with an internal pressure measuring circuit thereof attached to the catheter.

FIG. 1 shows a first embodiment of an internal pressure measuring device according to the present invention. In FIG. 1, reference numeral 10 denotes a pressure measuring catheter has an ordinary diameter and which is flexible and straight. The catheter 10 comprises a pressure measuring lumen 11 having an open distal end, a liquid charged lumen 12 whose closed distal end is disposed flush with the distal end of the lumen 11 and in which, for example, physiological saline 9 is charged, and an atmosphere-opened lumen 13 whose proximal end deviates from the catheter 10 and is made open to the atmosphere. The liquid-charged lumen 12 and the atmosphere-opened lumen 13 are manufactured by turning one lumen made of a synthetic resin and having an inner diameter of, for example. 0.5 mm. At that time, the inner compressed portion of the turned portion is notched to form a small hole 14 and thereby make the lumens 12 and 13 communicate with each other through the small hole 14, and the notched portion is then bonded.

The proximal end of the internal pressure measuring lumen 11 is connected to a pressure transducer 18 through one inlet 15a of a three-way cock 15. The liquid-charged lumen 12 is connected to a position correcting pressure transducer 19 through one inlet 16a of a three-way cock 16. These transducers 18 and 19 are mounted on a common base 17. The transducers 18 and 19 are both connected to an internal pressure measuring circuit portion 20 with a position correcting circuit attached thereto. The internal pressure measuring circuit portion 20 includes auto zero circuits 21 and 22 which automatically performs equilibrium operations based on the value converted from the pressure at that time when an auto zero switch is operated in a state where the pressure-receiving surfaces of the transducers 18 and 19 are opened to the atmosphere through the other inlets 15b and 16b by the manual operation of levers 15c and 16c of the three-way cocks 15 and 16, a correction circuit 23 for subtracting the output signal of the auto zero circuit 22 (which has a polarity of plus or minus) from the output signal of the auto zero circuit 21 output from the circuit 21 during the measurements, and a signal processing/output circuit 24 for processing the position-corrected internal pressure signal to display it on a Braun tube 25 or to record it on a recorder 26.

If the internal pressure measuring catheter 10 is used as the invasive blood pressure measuring device, it is inserted in an ordinary manner into a blood vessel 2 located closest to the pressure reference point (at the point of the tricuspid valve) of a chest 1. In this state, the proximal end of the atmosphere-opened lumen 13 led out from the chest 1 is open to the atmosphere, and the distal end surface of the physiological saline 9 is in contact with the atmosphere at the small hole 14. The inlets 15b and 16b are at the same level. Thereafter, automatic equilibrium operations of the auto zero circuits 21 and 22 are conducted by operating an auto zero switch in a state in which the pressure-receiving surfaces of the transducers 18 and 19 are opened to the atmosphere through the inlets 15b and 16b by manual operation of the levers 15c and 16c.

Blood pressure measurement begins when the levers 15c and 16c are returned to their original position. At that time, if the position of the base 17 is lower than that of the chest 1, the transducer 19 receives a pressure corresponding to the head between the distal end of the catheter 10 and the inlet 15b of the transducer 18, and the auto zero circuit 22 thus outputs a plus correction signal having a level corresponding to the pressure. This correction signal is subtracted by the correction circuit 23 from the blood pressure signal output from the auto zero circuit 21 on the basis of the electric signal detected and converted from the pressure by the transducer 18. The corrected blood pressure signal output from the correction circuit 23 is output to the signal processing/output circuit 24 and is displayed on the Braun tube 25 or recorded on the recorder 26.

During the measurement, the head of the catheter 10 may vary from its initial position due to changes in the position of the object to be measured. This change in the head is transmitted to the liquid-charged lumen 12, and the pressure received by the transducer 19 thus changes accordingly. Consequently, the correction signal output from the auto zero circuit 22 changes, thus making it possible for the blood pressure data to be monitored with a high degree of accuracy without being affected by changes in the position of the body. Furthermore, when the physiological saline 9 expands due to rise in the body temperature during the measurements, only the distal end surface thereof is displaced. The pressure value detected by the pressure measuring transducer merely changes by a value corresponding to the displacement of the height of the physiological saline 9. The distal end of the physiological saline 9 may advance slightly from the small hole 14. However, since the diameter of the lumen is small by itself, the physiological saline 9 can be held due to the surface tension.

When the inlets 15b and 16b are disposed above the pressure reference point of the chest 1 to which the base 17 is adjusted due to changes in the body position, the auto zero circuit 22 outputs a minus correction signal having a level corresponding to the pressure. This correction signal is subtracted by the correction circuit 23 from the actual blood pressure signal and thereby increases the level thereof.

The small hole through which the physiological saline 9 makes contact with the atmosphere may also be formed by drilling the adjoining surface of the distal end portions of the separately prepared liquid-charged and atmosphere-opened lumens whose distal end is closed. In that case, since the inner diameter of the lumen is small, the small hole has a diameter which allows the liquid to be held due to the surface tension thereof.

Even if the distal end surface of the physiological saline 9 does not face the small hole, the small hole may be small enough to allow the physiological saline 9 to be held due to the surface tension. Furthermore, to provide a position correction means which contains no circuit, as in the case disclosed by Japanese Patent Laid-Open No. 19132/1990, the internal pressure measuring lumen 11 and the liquid-charged lumen 12 may be connected to a single pressure differential transducer in place of the exclusive transducers. Furthermore, the present invention can also be applied to Swan-Ganz catheter in which the internal pressure measuring lumen is disposed at a position located behind the pressure reference point by a distance corresponding to the central venous pressure measuring position.

Figure 2:
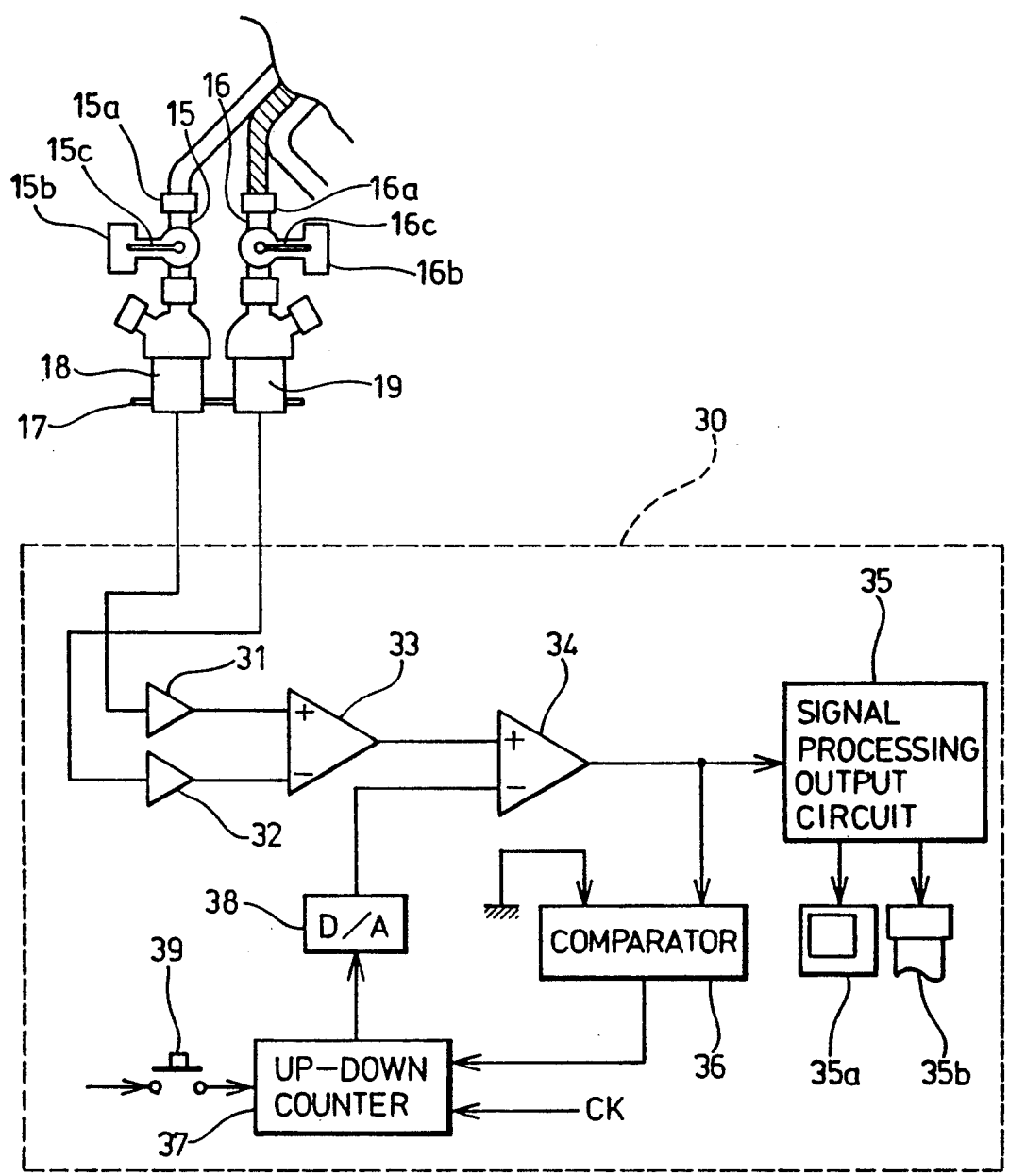
FIG. 2 shows a second embodiment of the present invention in which the internal pressure circuit portion has a common zero adjusting circuit.

FIG. 2 shows another embodiment of the present invention in which the internal pressure measuring circuit portion shown in FIG. 1 is constructed such that it contains a common zero adjusting circuit. In FIG. 2, the same reference numerals are used to denote parts which are the same as those of FIG. 1. The transducers 18 and 19 are mounted on the common base 17. The pressure-receiving surfaces of the transducers 18 and 19 can be made open to the atmosphere through the other inlets 16b and 16b by manually operating the levers 15c and 16c of the three-way cocks 15 and 16. The transducers 18 and 19 are connected to an internal pressure measuring circuit portion 30.

The internal pressure measuring circuit portion 30 includes a differential amplifier 33, serving as the position correcting subtraction means, for subtracting the amplified signal of an amplifier 32 for amplifying the detection signal of the transducer 19 from the amplified signal of an amplifier 31 for amplifying the detection signal of the transducer 18, a differential amplifier 34, serving as a zero adjusting subtraction means, for performing offset correction on the position-corrected internal pressure signal, and a signal processing/output circuit 35 for processing the position-corrected and zero-adjusted internal pressure signal and thereby displaying it on a Braun tube 35a or recording it on a recorder 35b. The differential amplifier 34 is connected to a zero adjustment value holding means which includes a comparator 36 for determining the polarity of the output signal of the differential amplifier 34 or whether or not the output signal has a zero level, an up-down counter 37 for counting up or down the input clock signal CK in accordance with the results of the determination made by the comparator 36, the counting being suspended at the zero level, and a D/A converter 38 for converting the counted value of the up-down counter 37 into an analog signal and for inputting the analog signal to one of the input terminals of the differential amplifier 34. The operation of the up-down counter 37 starts when an auto zero adjustment switch 39 is pressed. The up-down counter 37 holds its counted value until the auto zero adjustment switch 39 is pressed again.

The internal pressure measuring catheter 10 is inserted into the blood vessel 2 located closest to the pressure reference point (at the point of the tricuspid valve) of the chest 1. In this state, the proximal end of the atmosphere-opened lumen 13 led out from the chest 1 is open to the atmosphere, and the distal end surface of the physiological saline 9 is in contact with the atmosphere at the small hole 14. The inlets 15b and 16b are at the same level. Thereafter, the pressure-receiving surfaces of the transducers 18 and 19 are opened to the atmosphere through the inlets 15b and 16b by manually operating the levers 15c and 16c, by which the differential amplifier 33 outputs a zero adjustment value signal which is the results of the subtraction of the offset of the transducer 19 from the offset of the transducer 18. When the auto zero adjusting switch 39 is pressed in that state, automatic equilibrium operations of the up-down counter 37 starts. That is, the signal having an amplitude corresponding to the zero adjustment value is applied to one of input terminals of the differential amplifier 34. Automatic equilibrium operation is ended when the comparator 36 detects the zero level.

Blood pressure measurement begins when the levers 15c and 16c are returned to their original position. Consequently, the transducer 19 receives a pressure corresponding to the head between the distal end of the internal pressure measuring catheter 10 and the inlet 15b of the transducer 18, and the differential amplifier 33 outputs a position-corrected internal pressure signal. At this time, if the position of the base 17 is lower than that of the chest 1, the pressure received by the transducer 19 is positive, while if the base 17 is disposed above the chest 1, the transducer 19 receives a corresponding negative pressure. The output signal of the differential amplifier 33 is zero adjusted by the differential amplifier 34 on the basis of the zero adjustment value held by the up-down counter 37. The resultant actual blood pressure signal is output to the signal processing/output circuit 35 and is thereby displayed on the Braun tube 35a or recorded on the recorder 35b as the blood pressure data.

To manually conduct zero adjustment in the above-described embodiment, a variable resistor is connected as the zero adjustment value holding means to one of the input terminals of the differential amplifier 34. Alternatively, auto zero adjustment operation may be started by operating a valve without using the auto zero adjustment switch 39.

Figure 3:
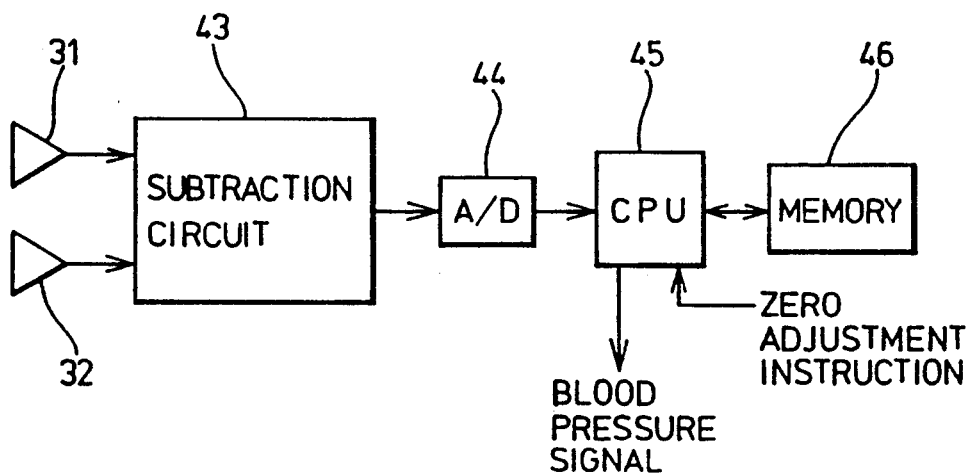
FIG. 3 shows a modification of the common zero adjustment type internal pressure measuring circuit portion.

FIG. 3 shows a modification of a common zero adjustment type internal pressure measuring circuit portion. The same reference numerals are used to denote parts which are the same as those of the aforementioned embodiment. That is, an analog subtraction circuit 43, serving as the position correction subtraction means, is connected to an A.D converter 44 for converting the output signal of the subtraction circuit 43 into a digital signal, which is in turn connected to a central processing circuit 45 which serves as the zero adjustment subtraction means. A memory 46 for storing the offset differential calculated by the subtraction circuit 43 is connected to the CPU 45 as the zero adjustment value holding means. During the measurement, the CPU 45 subtracts the zero adjustment value (which may be a plus or minus value) stored in the memory 46 from the position-corrected output signal of the subtraction circuit 43, and outputs an internal pressure signal.

Figure 4:
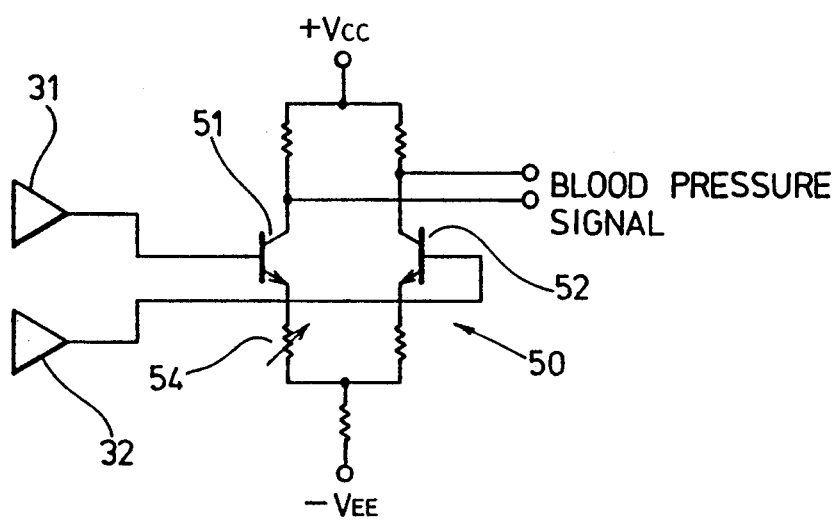
FIG. 4 shows another modification of the common zero adjustment type internal pressure measuring circuit.

FIG. 4 shows another modification of the common zero adjustment type internal pressure measuring circuit portion. In this example, the position correcting and zero adjusting subtraction means are constructed by a common differential amplifier 50 which uses transistors 51 and 52. A serial resistor of the emitter of the transistor 51 is constituted by a variable resistor 54 which serves as the zero adjustment value holding means. Zero adjustment is conducted by manually operating the variable resistor 54 such that the differential output signal is zero. During the measurement, zero adjustment is conducted in accordance with the value set by the variable resistor 54 when subtraction is made in the differential amplifier 50 on the output signals of the transducers 18 and 19.

Figure 5:
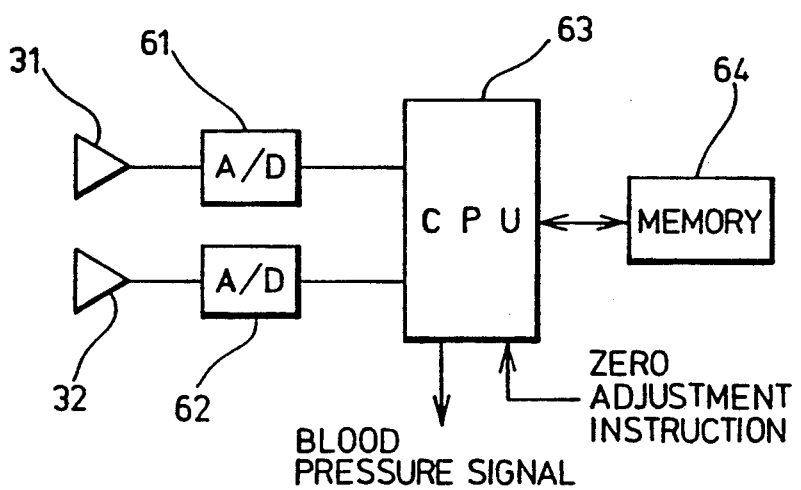
FIG. 5 shows still another modification of the common zero adjustment type internal pressure measuring circuit.

FIG. 5 shows still another modification of the common zero adjustment type internal pressure measuring circuit portion. In this example, the output signals of the amplifiers 31 and 32 for the transducers 18 and 19 are respectively converted into digital signals by A/D converters 61 and 62, and are then supplied to a central processing unit 63 serving as the position correcting and zero adjustment value holding means. A memory 64 stores a offset differential as the zero adjustment value (which may be a plus or minus value). During the measurement, the CPU 63 performs both position correction and zero adjustment to produce an internal pressure signal.

What is claimed is:

1. An internal pressure measuring device comprising:
   an internal pressure measuring catheter constituted by at least three lumens which are an internal pressure measuring lumen whose distal end is open, a position correcting liquid-charged lumen whose distal end is closed and in which a liquid is charged, and a position correcting atmosphere-opened lumen whose proximal end is open to the atmosphere, said three lumens having adjoining peripheral surfaces, the liquid being brought into contact with the atmosphere at the distal end of said liquid-charged lumen and of said atmosphere-opened lumen;
   an internal pressure measuring transducer connected to a proximal end of said internal pressure measuring lumen and a pressure measuring transducer connected to a proximal end of said position correcting liquid-charged lumen, both of said internal pressure measuring transducer and said pressure measuring transducer being mounted on a common base; and
   an internal pressure measuring circuit portion for performing position correction on the output signal of said internal pressure measuring transducer using the output signal of said pressure measuring transducer to detect an internal pressure signal and for outputting the obtained internal pressure value to a display device or to a recording device,
   wherein the adjoining surfaces of the distal end portions of said liquid-charged lumen and said atmosphere-opened lumen have a small hole through which the charged liquid can be brought into contact with the atmosphere through said atmosphere-opened lumen.

2. The internal pressure measuring device according to claim 1, wherein said small hole is formed by turning a single lumen to form said liquid-charged lumen and said atmosphere-opened lumen and by making said two lumens communicate with each other at the turned portion.

3. The internal pressure measuring device according to claim 1, wherein said small hole is formed by drilling the adjoining surfaces of the distal end portions of separately prepared liquid-charged lumen and atmosphere-opened lumen whose distal end is closed.

4. The internal pressure measuring device according to claim 1, wherein said internal pressure measuring circuit portion includes a position correcting subtraction means for subtracting the output signal of said pressure measuring transducer from the output signal of said internal pressure measuring transducer, a zero adjustment value holding means for holding as a zero adjusting value the output signal of said subtraction means when said two transducers are zero adjusted, and a zero adjustment subtraction means for outputting an internal pressure signal by subtracting the zero adjusting value held by said zero adjusting value holding means from the output signal of said subtraction means which is output during the measurement.

5. The internal pressure measuring device according to claim 4, wherein said zero adjustment subtraction means and said position correcting subtraction means are the same.

* * * * *